United States Patent
Heimberger

(10) Patent No.: US 9,089,297 B2
(45) Date of Patent: Jul. 28, 2015

(54) URETERO-RENOSCOPE

(75) Inventor: Rudolf Heimberger, Oberderdingen (DE)

(73) Assignee: Richard Wolf GmbH, Knittlingen (DE)

( * ) Notice: Subject to any disclaimer, the term of this patent is extended or adjusted under 35 U.S.C. 154(b) by 639 days.

(21) Appl. No.: 12/726,440

(22) Filed: Mar. 18, 2010

(65) Prior Publication Data

US 2010/0240950 A1    Sep. 23, 2010

(30) Foreign Application Priority Data

Mar. 18, 2009    (DE) .................. 10 2009 013 312

(51) Int. Cl.
*A61B 1/00*    (2006.01)
*A61B 1/307*    (2006.01)

(52) U.S. Cl.
CPC ............... *A61B 1/307* (2013.01); *A61B 1/0008* (2013.01)

(58) Field of Classification Search
CPC .......... A61B 1/00089; A61B 1/00101; A61B 1/00137

USPC ......... 600/104, 112, 114, 121–123, 129, 164, 600/175, 106, 127

See application file for complete search history.

(56) References Cited

U.S. PATENT DOCUMENTS

| | | | |
|---|---|---|---|
| 5,542,924 A * | 8/1996 | Snoke et al. ................ 604/23 |
| 2005/0107663 A1* | 5/2005 | Saadat et al. ............... 600/104 |
| 2005/0272975 A1* | 12/2005 | McWeeney et al. ........ 600/154 |
| 2006/0111612 A1* | 5/2006 | Matsumoto .................. 600/127 |
| 2006/0173244 A1 | 8/2006 | Boulais et al. |
| 2006/0200000 A1* | 9/2006 | Sato et al. .................... 600/146 |
| 2007/0197875 A1* | 8/2007 | Osaka .......................... 600/109 |
| 2008/0058586 A1* | 3/2008 | Karpiel ........................ 600/127 |
| 2009/0048486 A1 | 2/2009 | Surti |
| 2009/0147076 A1* | 6/2009 | Ertas ............................ 348/65 |
| 2011/0157574 A1* | 6/2011 | Kato et al. ................... 355/71 |

* cited by examiner

*Primary Examiner* — Thomas J Sweet
*Assistant Examiner* — Kevin G Barry, III
(74) *Attorney, Agent, or Firm* — Panitch Schwarze Belisario & Nadel LLP

(57) ABSTRACT

A uretero-renoscope includes a shaft, on whose distal end an instrument head is arranged. The instrument head tapers continuously in the distal direction.

7 Claims, 3 Drawing Sheets

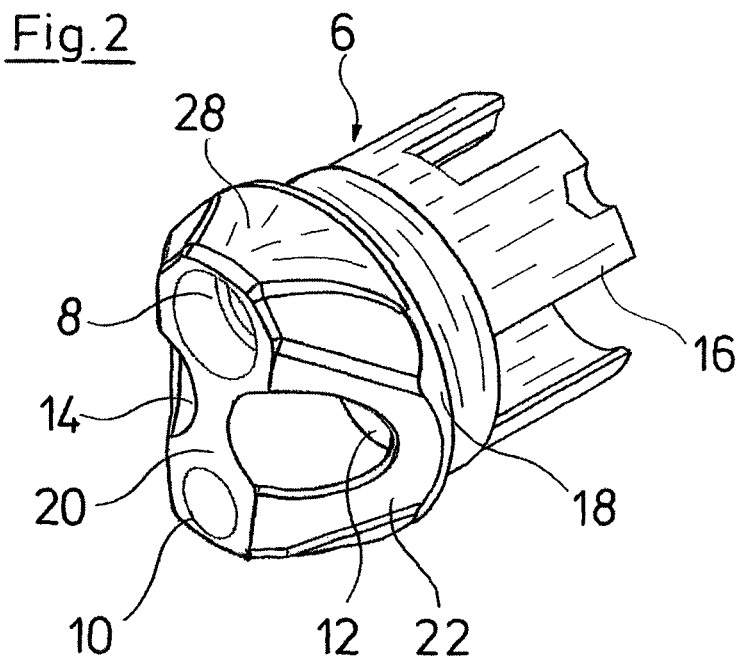
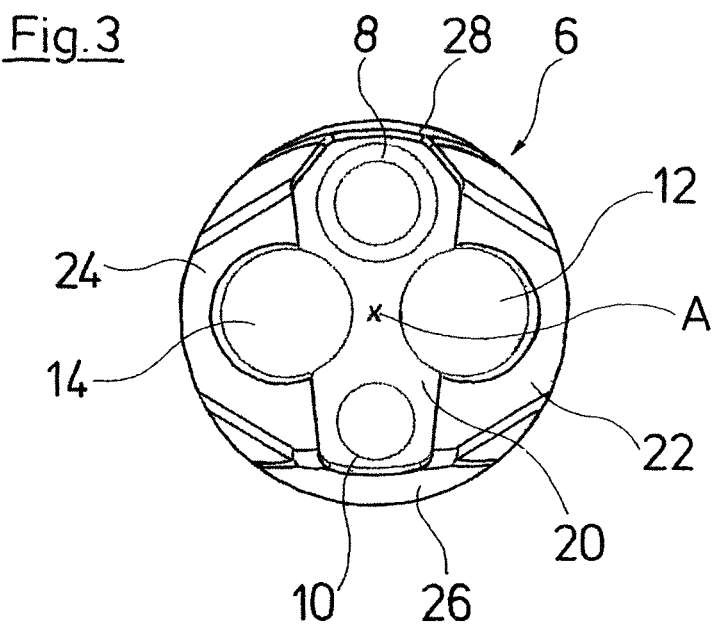

URETERO-RENOSCOPE

BACKGROUND OF THE INVENTION

The present invention relates to a uretero-renoscope.

Uretero-renoscopes serve for the transurethral diagnosis and therapy in the region of the ureter and renal pelvis. Often, these instruments are applied for removing urinary stones from the ureter or from the renal calix group. For this, the hollow shaft of the uretero-renoscope, which is mostly designed in a flexible manner proceeding from the mouth of the ureter, is introduced up to the urinary stone in the urethra, where the urinary stone may either be directly removed with a stone gripper receptacle led through the hollow shaft, or in the case of larger stones, is reduced in size prior to this, for example, by way of a laser probe (laser tube). It is particularly with very narrow-lumen ureters or with narrowings in the urethra, e.g. ureter strictures, that the danger exists of the mucous membrane tissue surrounding the ureter being traumatized or even perforated on introducing the uretero-renoscope.

Against this background, it is the object of the invention to provide a uretero-renoscope, which may be moved in the ureter such that it is gentler to tissue.

BRIEF SUMMARY OF THE INVENTION

The uretero-renoscope according to one aspect of the present invention includes a shaft. Here, it is the case of a hollow shaft which may be designed in a rigid as well as flexible manner. However, a flexible design of the hollow shaft is preferred, so that the hollow shaft may be bent transversely to its longitudinal extension. An instrument head is arranged at the distal end of the hollow shaft. This instrument head may be part of the hollow shaft or, as a separate part, may be fastened on the distal end of the hollow shaft. Guide channels for observation optics and for illumination means run out at the instrument head. Moreover, also at least one instrument channel for an instrument applied for therapy purposes, may run out at the instrument head.

The basic idea of the invention is to design the instrument head of the uretero-renoscope according to the invention such that it tapers in the distal direction. Accordingly, the instrument head has its smallest cross section at its distal end, the cross section widening proximally in a stepless manner to a largest cross section, wherein this largest cross section of the instrument head usefully and basically corresponds to the cross section of the hollow shaft. This design of the instrument head is advantageous inasmuch as the uretero-renoscope according to the present invention may penetrate into the ureter and advance in the urethra, in a manner which is more gentle to the mucous membrane tissue and with less resistance, in comparison to the uretero-renoscopes which have been known until now, wherein it widens the ureter in an atraumatic manner like a dilator. The danger of tissue traumatization or perforation is significantly reduced by way of this.

Basically, the way in which the instrument head continuously tapers is infinite. Thus the instrument head may taper in a conical or prismatic manner or may taper conically in at least one part peripheral section and/or taper in straight beveled manner in at least one other part peripheral section. Preferably, the instrument head tapes in a wedge-like manner at two peripheral sections which are essentially diametrically distant to one another. Accordingly, the instrument head may be beveled in each case at two peripheral sections which are directly distant to one another, in a manner such that the peripheral surface in these peripheral sections of the instrument head forms two straight planes, which are beveled with respect to the middle axis of the instrument head, such that they taper in a more or less pointed manner in the distal direction to the middle axis of the instrument head.

Usefully, the instrument head does not taper in a manner such that its distal end forms an apex point or apex edge. Instead of this, an end-face is preferably formed at the distal end of the instrument head, which is typically aligned perpendicularly to the middle axis of the instrument head. This means that although the instrument head tapers in a distal manner, the distal end of the instrument head is designed in an atraumatically blunt manner on account of the end-face.

Preferably, the guide channel for the observation optics and the guide channel for the illumination means run out at the end-face forming the distal end of the instrument head. Accordingly, these instrument parts are arranged at a location at which the observation field of the observation optics and the illumination field of the illumination means may not be restricted by other regions of the instrument head. The guide channels for the observation optics and the illumination means may be closed at the end-face by way of transparent end-widows and/or lenses, which are arranged there. Moreover, it may also be advantageous if the complete end-face is formed by a cover, which covers the optics and the illumination means and which is transparent at least in this region.

Uretero-renoscopes for therapy purposes, as a rule, comprise at least one instrument channel which is led through the instrument and through which an auxiliary instrument may be led to the field of operation. At least such an instrument channel is also usefully provided with the uretero-renoscope according to the present invention. This runs out preferably at one of the peripheral sections which are designed beveled in a wedge like manner. The instrument channel may also be arranged such that its clearance envelope lies completely in the region of this peripheral section designed in a beveled manner. The instrument channel is typically to be arranged as close as possible to the observation optics and the illumination means, in order to ensure that an instrument led through the instrument channel is located in the field of viewing or field of illumination of the optics and illumination means respectively, arranged at the distal end-face of the instrument head. For this purpose, the instrument channel with the uretero-renoscope according to the present invention is preferably arranged in a manner such that it intersects (cuts) the transition edge from the beveled peripheral section to the end-face of the instrument head.

The uretero-renoscope according to the present invention particularly advantageously comprises two instrument channels, wherein preferably in each case one instrument channel runs out at one of the two peripheral sections which are designed beveled in a wedge-like manner. This design renders the uretero-renoscope according to the present invention suitable, in particular for the lithotripsy of urinary stones. Whilst on destroying larger urinary stones with a uretero-renoscope with only one instrument channel, it is necessary to remove a probe used for the destruction of the urinary stones, out of the instrument channel, in order to be able to lead a stone gripper receptacle for receiving urinary stones fragments, to the field of operation, the presence of two instrument channels permits the probe for destroying urinary stones to be left in one of the instrument channels. Accordingly, an otherwise constantly required exchange of probe and stone gripper receptacle in an instrument channel may be done away with, which means a significant saving of time with an operation to remove urinary stones. The operator, as well as the patient, is significantly relieved by way of this. As described above, the two instrument channels are usefully arranged such that they in each case intersect the transition edge of the respective beveled peripheral section to the end-face of the instrument head.

The instrument head may advantageously also taper in the distal direction at least one peripheral section arranged between the wedge-like peripheral sections, in order to further improve the dilatation characteristics of the uretero-renoscope according to the present invention. For this purpose, this peripheral section may be beveled in a prismatically straight manner, or taper in a conical manner as is preferably envisaged.

Laser probes are particularly suitable as lithotripters with the transurethral removal of urinary stones. The application of a laser probe led through an instrument channel is also envisaged with the uretero-renoscope according to the present invention. Advantageously, this laser probe may be fixed on a control housing connecting at the proximal side onto the shaft of the uretero-renoscope. One may prevent the laser probe from undesirably displacing within the shaft by way of this measure, which with an unintended activation of the laser probe, as the case may be, may lead to a destruction of the shaft. The fixation ability of the laser probe on the control housing is favorable inasmuch as the control housing per se serves for handling the uretero-renoscope.

The laser probe is preferably displaced in a limited manner in the longitudinal direction of the instrument channel in this instrument channel. In this context, a displacement path of the laser probe from a working position outside the instrument channel into a position within the instrument channel and vice versa may be provided, wherein the position within the instrument channel is advantageously selected such that an unintended activation of the laser does not destroy the instrument.

Further advantageously, with the uretero-renoscope according to the present invention, at least one instrument channel may form a rinsing channel. For example, this instrument channel may be connected to a rinsing fluid supply conduit. For this, a suitable connection may be provided on the control housing. A rinsing fluid may be led to the field of operation via this connection and, as the case may be, may be led back again from there.

One may achieve particularly large rinsing fluid volume flows if the uretero-renoscope comprises two instrument channels, which both form a rinsing channel, wherein the rinsing fluid is led via both instrument channels to the field of operation and may be led back again from there. However, only an intermittent rinsing is possible in this manner. In order to be able to create a permanent rinsing, one further preferred design of the uretero-renoscope envisages designing one instrument channel as a rinsing fluid feed, and the second instrument channel as a rinsing fluid return.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

The invention is hereinafter explained in more detail by way of one embodiment example represented in the drawing. There are shown in the drawings:

FIG. 2 is a schematic perspective view of an instrument head of the uretero-renoscope shown in FIG. 1;

FIG. 3 is a front elevation view of the instrument head shown in FIG. 2;

DETAILED DESCRIPTION OF THE INVENTION

Figure 1:
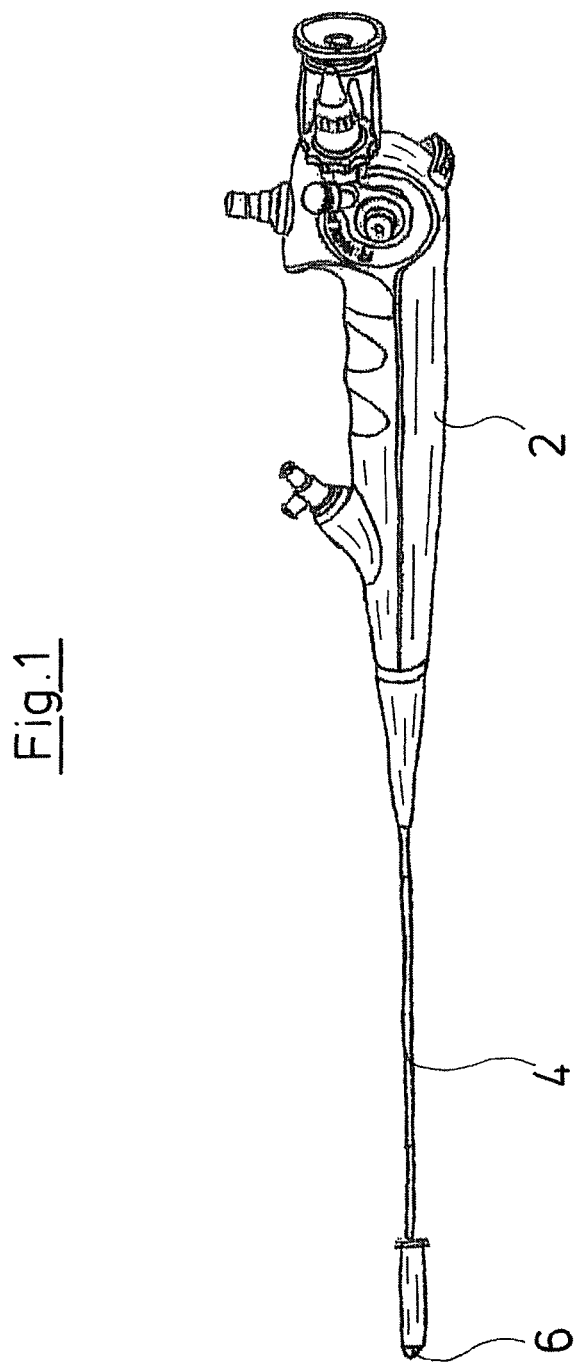
FIG. 1 is a schematic perspective view of a uretero-renoscope in accordance with a preferred embodiment of the present invention, wherein a distal shaft end is shown enlarged.
Figure 4:
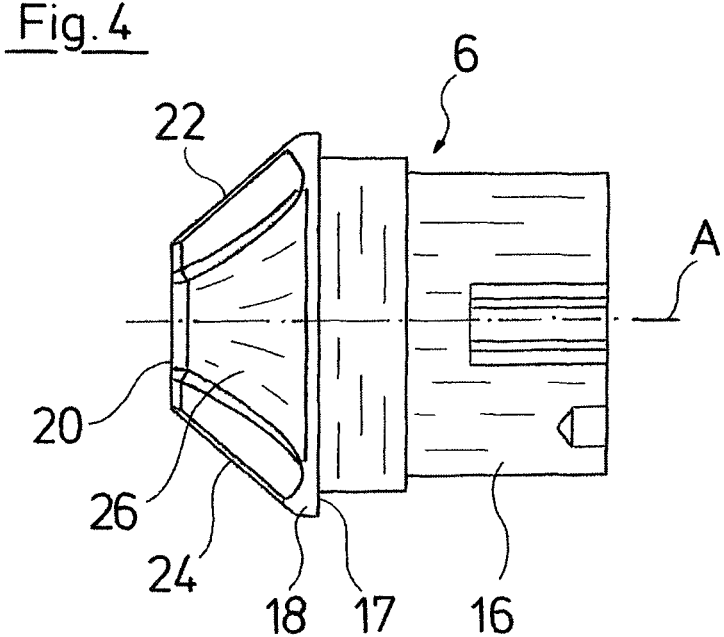
FIG. 4 is a side elevation view of the instrument head shown in FIG. 2.
Figure 5:
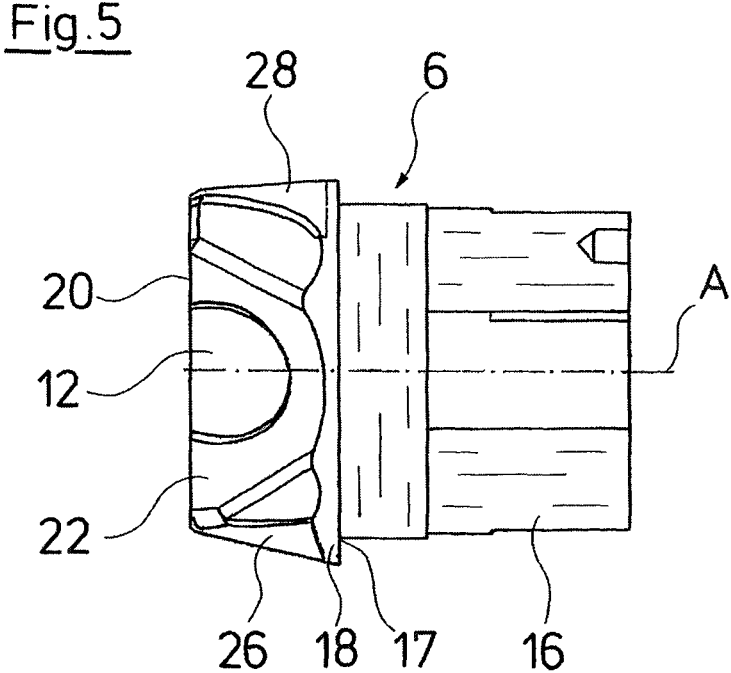
FIG. 5 is a side elevation view of the instrument head shown in FIG. 2 rotated by 90° with respect to FIG. 4.

Certain terminology is used in the following description for convenience only and is not limiting. The words "first" and "second" designate an order or operations in the drawings to which reference is made, but do not limit these steps to the exact order described. Additionally, the terms "a," "an" and "the," as used in the specification, mean "at least one." The terminology includes the words above specifically mentioned, derivatives thereof, and words of similar import.

Referring to the drawings in detail, wherein like numerals indicate like elements throughout, there is shown in FIGS. 1-5 a preferred embodiment of a uretero-renoscope in accordance with the present invention. The uretero-renoscope represented in FIG. 1 preferably includes a control housing 2 serving for handling the instrument, on whose distal end a shaft 4 is arranged. The shaft 4 is preferably designed as a flexible hollow shaft. An instrument head 6 is preferably arranged at the distal end of the shaft 4.

Proceeding from the control housing 2, a guide channel 8 for the illumination means, a guide channel 10 for an observation optics as well as two instrument channels 12 and 14, all of which not being shown in FIG. 1, preferably extend through the shaft 4, wherein the guide channels 8 and 10 as well as the instrument channels 12, 14 preferably all run out at the instrument head 6 (See FIGS. 2 and 3). A laser probe for smashing urinary stones, which may be fixed in the control housing 2, may be led in one of the instrument channels 12, 14 for removing urinary stones, wherein however this laser probe is not represented. The other instrument channel 12, 14 may then serve as an access for a stone gripper receptacle which is likewise not represented, and which may be led through the instrument channel 12, 14 to the field of operation The instrument head 6 preferably includes a section 16, which is preferably unreleasably fixed in the distal end of the shaft 4. A section 18 of the instrument head 6 preferably connects distally of this section 16 whilst forming a shoulder 17, and this section 18 is preferably arranged distally outside the shaft 4 when the section 16 is fixed in the shaft 4. The shoulder 17 is preferably dimensioned such that the instrument head 6 on the shoulder 17 has the same outer cross section as the shaft 4, thus is flush with the shaft 4 there.

In the region of the section 18, the cross section of the instrument head 6 preferably reduces continuously in the distal direction to an end-face 20, which forms the distal end of the instrument head 6. Inasmuch as this is concerned, the instrument head 6 quasi forms a dilator, with which the ureter may be widened in a manner which is gentle to the tissue.

The cross section of the end-face 20 is preferably significantly smaller than the distal end section of the shaft 4. For example, the instrument head 6 preferably tapers in the direction of its distal end or towards the end-face 20. This tapering is essentially caused by way of the two peripheral sections 22, 24 of the instrument head 6, which are distanced diametrically to one another, tapering to one another in a pointed and wedge-like manner in the form of plane surfaces, wherein they have essentially the same inclination angle (FIG. 4) with respect to a middle axis A of the instrument head 6. Moreover, the instrument head 6 preferably also tapers in the region of the peripheral sections 26, 28, which lie between the peripheral sections 22, 24. However, the tapering of the instrument head 6 in the peripheral sections 26, 28 is preferably effected conically or with a curved peripheral surface of these peripheral sections 26, 28, wherein the peripheral surface in the region of the peripheral section 26 tapers to the middle axis A of the instrument head 6 in the distal direction greater than in the region of the peripheral section 28.

The guide channel 8 of the observation optics preferably runs out at the end-face 20, in an edge region bordering the peripheral section 28, whilst the guide channel 10 for the illumination means preferably runs out in an edge region of the end-face 20, which borders the peripheral section 26.

The instrument channel 12 is preferably arranged such that it exits the instrument head 6 mainly in the region of the periphery section 22, wherein however it intersects the end-face 20 in an edge region which borders the peripheral section 22 and which lies between the guide channel 8 of the observation optics and the guide channel 10 of the observation optics. Corresponding to this, the instrument channel 14 preferably exits from the instrument head 6 such that its opening intersects the peripheral section 24 as well as an edge region of the end-face 20 bordering thereon, between the guide channel 8 of the observation optics and the guide channel 10 of the illumination means. One ensures that the instruments led through the instrument channels 12, 14 are brought into the observation field and illumination field of the observation optics and of the illumination means by way of this arrangement of the instrument channels 12, 14 in the direct vicinity of the guide channel 8 of the observation optics and of the guide channel 10 of the illumination means.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A uretero-renoscope comprising:
a shaft (4) defining a longitudinal axis (A); and
an instrument head (6) on a distal end of the shaft (4) and defining a middle axis generally coaxial with the longitudinal axis, the instrument head (6) including:
a proximal portion (16) fixed in the distal end of the shaft (4),
an end face (20), perpendicular to the middle axis, forming a distal end of the instrument head (6), including a guide channel (8) for observation optics and a guide channel (10) for illumination means, the guide channels (8, 10) being symmetrically disposed about the longitudinal axis (A),
opposing first and second peripheral sections (22, 24) essentially diametrically distant to one another about the middle axis, each of the first and second peripheral sections (22, 24) being beveled in a wedge-shaped manner from the proximal portion (16) to the end face (20), wherein an instrument channel (12, 14) extends through each one of the first and second peripheral sections (22, 24), the instrument channels (12, 14) being symmetrically disposed about the longitudinal axis (A), and
opposing third and fourth peripheral sections (26, 28), each of the third and fourth peripheral sections (26, 28) arranged between the first and second peripheral sections (22, 24) and distally tapering from the proximal portion (16) to the end face (20), wherein the third peripheral section (26) distally tapers further toward the middle axis than the fourth peripheral section (28).

2. The uretero-renoscope according to claim 1, wherein a laser probe is guided in one of the instrument channels (12, 14) and may be fixed on a control housing (2) bordering the shaft (4) on a proximal side.

3. The uretero-renoscope according to claim 2, wherein the laser probe is displaceable in one of the instrument channels (12, 14) in a limited manner in a longitudinal direction of the instrument channels (12, 14).

4. The uretero-renoscope according to claim 1, wherein at least one of the instrument channels (12, 14) forms a rinsing channel.

5. The uretero-renoscope according to claim 1, wherein one of the instrument channels (12, 14) forms a rinsing fluid feed and the other one of the instrument channels (12, 14) forms a rinsing fluid discharge.

6. A uretero-renoscope comprising:
a shaft (4) defining a longitudinal axis (A);
an instrument head (6) at a distal end of the shaft (4) and defining a middle axis generally coaxial with the longitudinal axis, the instrument head (6) including:
a proximal portion (16) having an outer periphery,
an end-face (20) forming a distal end of the instrument head (6), including a guide channel (8) for observation optics and a guide channel (10) for illumination means, the guide channels being symmetrically disposed about the longitudinal axis (A),
first and second peripheral sections (22, 24) extending from the distal end of the shaft (4) to the end-face (20),
third and fourth peripheral sections (26, 28) extending from the distal end of the shaft (4) to the end face (20),
each of the first and second peripheral sections (22, 24) tapering at a constant angle to the end-face (20),
each of the third and fourth peripheral sections (26, 28) being positioned between the first and second peripheral sections (22, 24), each of the third and fourth peripheral sections (26, 28) having a curved peripheral surface, and the third peripheral section (26) distally tapering further toward the middle axis than the fourth peripheral section (28); and
two spaced-apart instrument channels (12, 14) extending through the shaft (4) and the instrument head (6), and being symmetrically disposed about the longitudinal axis (A), each instrument channel (12, 14) being positioned at least partially in one of the first and second peripheral sections (22, 24) at the instrument head (6).

7. The uretero-renoscope according to claim 6, wherein the two guide channels (8, 10) are each positioned at least partially in one of the third and fourth peripheral sections (26, 28) at the instrument head (6).

* * * * *